Figure 3:
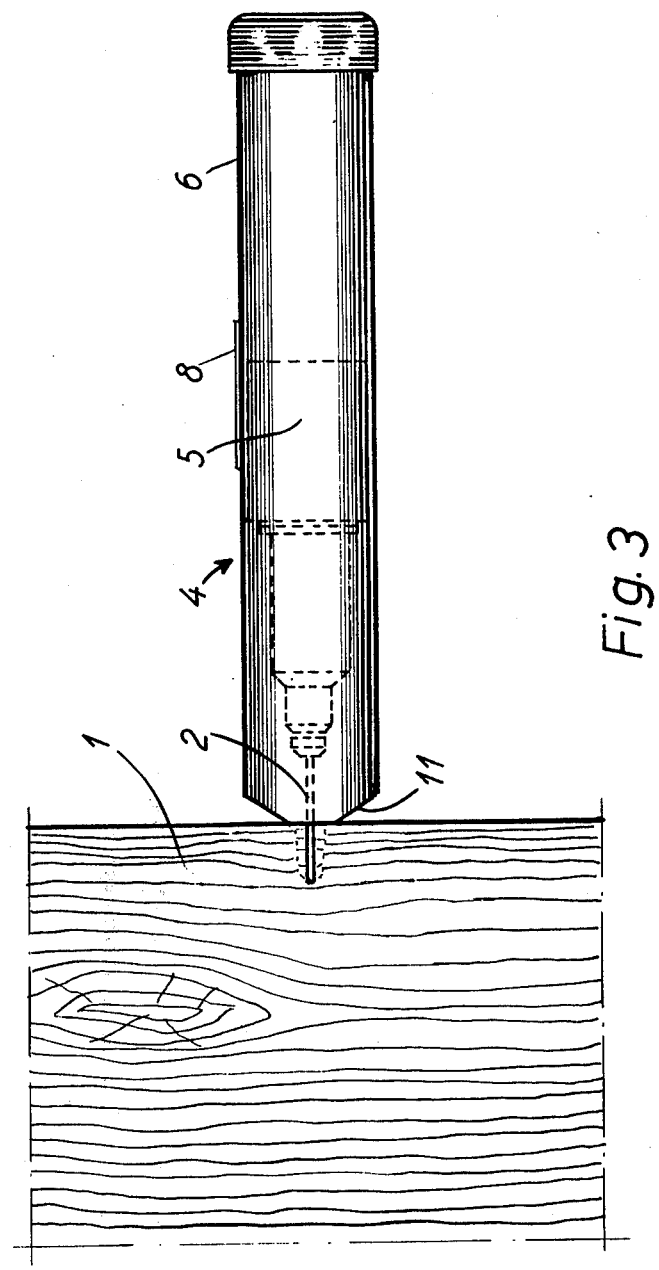

United States Patent [19]

Hoffmeyer

[11] 4,182,163

[45] Jan. 8, 1980

[54] METHOD AND APPARATUS FOR MEASURING THE STRENGTH OF A FIBROUS BODY

[75] Inventor: Preben Hoffmeyer, Hilleroed, Denmark

[73] Assignee: Wood-Slimp GmbH, Chur, Switzerland

[21] Appl. No.: 898,695

[22] Filed: Apr. 21, 1978

Related U.S. Application Data

[63] Continuation of Ser. No. 718,358, Aug. 27, 1976, abandoned.

[30] Foreign Application Priority Data

Sep. 3, 1975 [DK] Denmark .............................. 3943/75

[51] Int. Cl.² ............................................... G01N 3/48
[52] U.S. Cl. ...................................................... 73/82
[58] Field of Search ................ 73/82, 81, 85, 12, 88 C

[56] References Cited

U.S. PATENT DOCUMENTS

| 881,047 | 3/1908 | Ballentine | 73/82 |
|---|---|---|---|
| 2,321,770 | 6/1943 | Persson | 73/81 |
| 2,975,631 | 3/1961 | Hansen | 73/81 |
| 3,498,120 | 3/1970 | MacMillan | 73/81 |
| 3,732,725 | 5/1973 | Allen et al. | 73/81 |

OTHER PUBLICATIONS

Soiltest, "The Concrete Test Hammer", Ready Mixed Concrete, Aug. 1966, (4 pages).

Primary Examiner—Anthony V. Ciarlante
Attorney, Agent, or Firm—Burgess, Ryan and Wayne

[57] ABSTRACT

The strength of a material is measured by positioning a tool against a surface of the material and driving an elongated piercing plug having a blunt front end into the material. The penetration depth of the piercing plug is proportional to the material strength. A trigger on the tool for releasing the piercing plug for driving movement into the material requires manual force acting through the trigger on the tool in a direction for maintaining the front end portion of the tool in engagement with the surface of the material being tested.

11 Claims, 3 Drawing Figures

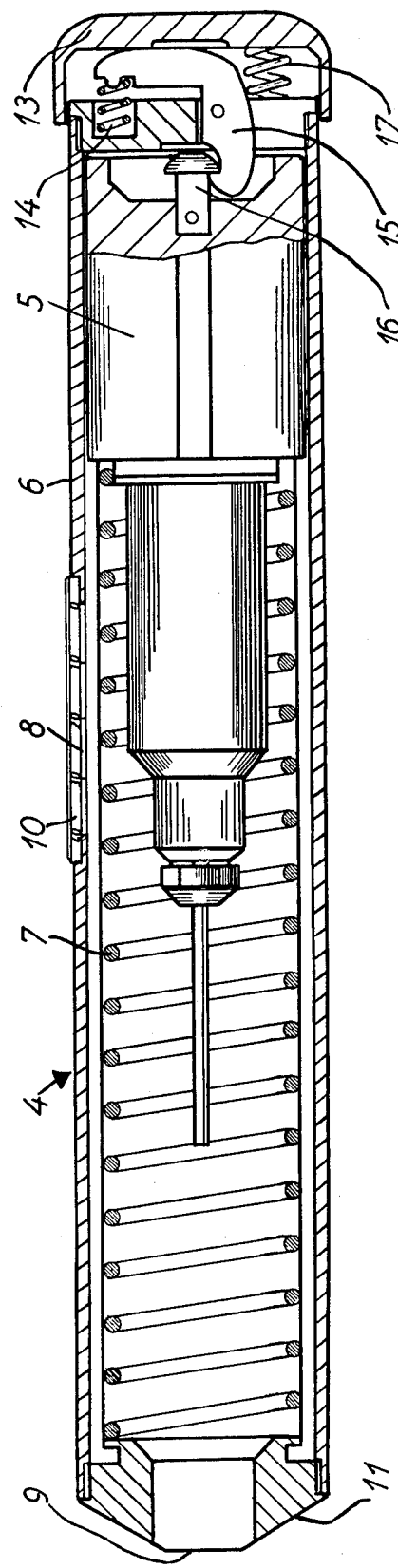
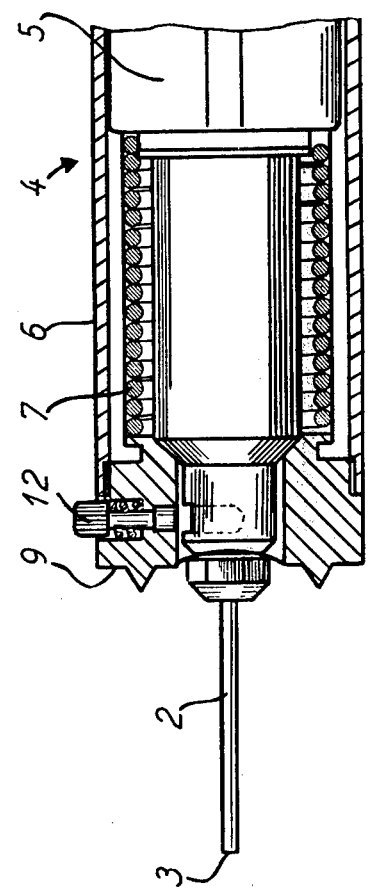
Fig. 1
Fig. 2

METHOD AND APPARATUS FOR MEASURING THE STRENGTH OF A FIBROUS BODY

This is a continuation of application Ser. No. 718,358 filed Aug. 27, 1976 now abandoned. The parent application having a priority date of Sept. 3, 1975, based on corresponding Application Ser. No. 3943/75 Denmark.

The application relates to an apparatus for measuring the strength of a body, such as a wooden material.

Various methods for testing the strength of a body, such as a wooden material, by mechanical stressing of the material, are known. A pointed object can be pressed into it with a constant power and the penetration be judged. Furthermore drill samples can be taken, the compressive strength of which can then be measured. These two methods, however, have proved to be too undependable. Furthermore the rigidity of the material can be measured, where practically feasible, by exposing the material to a given load and the strength be determined on a basis of the deflection. This method is, however, very difficult to carry out in practise.

Finally the impact strength of the material can be determined. This method is the preferred one, as the impact strength has proved to be an indicator of the mechanical properties of the material, which depends on the degree of disintegration of the material and its density. The impact strength thus largely depends on the general condition of the material. Disintegration by biological or bacterial means e.g. means a marked fall of the impact strength. Furthermore the impact strength strongly depends on the density of the material. And finally the impact strength is practically independent on the contents of water of the material.

Hitherto known measurings of the impact strength have been made in laboratories on small prisms, taken from the material and placed in a special testing machine, in which the prism is exposed to a combined dynamical bending and tensile stress. This method is often inexpedient as it partly demands that one or several samples are taken, and partly that the measuring must be made on a machine in a laboratory. Furthermore it weakens the material and it is a costly and time-consuming method.

The object of the invention is to remedy these drawbacks of the known method, and this is according to the invention achieved by driving a penetration body by means of a suitable quantity of energy, being released momentarily, into the material, after which the penetration of the penetration body into the material can be measured as a direct indication of the strength of the material.

In the first place is hereby achieved that the measuring can be made in situ. Furthermore a direct determination of the strength immediately after the impact is achieved, as the penetration of the penetration body depends on all the factors, which are of importance to the mechanical properties of the material. There is, therefore, a direct connection between the strength and the degree of penetration. As the penetration of the piercing plug can be read off directly after the driving in, there is in addition achieved, the benefit that the operators can make supplementary measurings, where zones appear, which may require a further examination. Furthermore the material is not spoiled by this method as no samples have to be taken.

By using a spring driven impact hammer, the result of the measuring is made independent on the operators, as the impact hammer contains a well defined kinetic energy, which is uniform by each impact.

It is suitable to the purpose to use the impact hammer where an inertia body is linearly driven by a spring, and the drive arrangement of which is simple and steady, and by making the trigging conditioned on a given pressure on the impact hammer, a constant pre-pressure is achieved for the driving in before the impact. This will secure uniform conditions of the driving in.

In using the piercing plug with a blunt front end, surfaces of fracture are produced during the penetration of the piercing plug into the material as a result of a combined dynamical bending stress and a dynamical tensile stress of the fibres of the wood. This stressing thus corresponds closely to a normal testing of the impact strength in a laboratory.

To be able to read off the penetration of the piercing plug into the material it is suitable to the purpose to provide the casing with an opening opposite to the inertia body and, to place a scale in the opening so that the penetration depth and with that, the strength can be determined.

By the determination of the strength of e.g. a buried post it is finally suitable to the purpose that the front end of the impact hammer casing has been obliquely cut, so that testings of the strength of the post in the area immediately under the surface of the ground can be made without having first to remove large quantities of earth.

The invention will be explained in further details below with reference to the drawing in which FIG. 1 shows an impact hammer in side elevation in section, FIG. 2 shows the impact hammer in its advanced position and FIG. 3 shows the impact hammer in process of being driven into a wooden material.

The apparatus for use in performance of the method can be designed as shown in FIGS. 1 and 2. It consists of an impact hammer 4 which has outermost a casing 6, which in front is provided with a front piece 9 and to the rear with a trigger arrangement. The casing 6 is suitably shaped like a cylindrical pipe, into which the impact arrangement can be built in. This impact arrangement consists of an inertia body 5 which in front is provided with a retaining member, to which a penetration body or piercing plug 2 can be attached. The forward motion of the inertia body 5 causes that the piercing plug 2 is led out through an opening in the front piece 9, a maximum distance until the retaining member rests against the inner side of the front piece, as shown in FIG. 2.

To the front of the inertia body 5 is attached a tension spring 7, the opposite end of which is attached to the front end of the casing at the front piece 9. In the compressed position of the spring 7, i.e. in its relaxed position, as shown in FIG. 2, the piercing plug 2 is most advanced. By carrying the inertia body 5 back into the casing 6, the spring 7 is loaded. In order to keep the impact arrangement in its loaded position, as shown in FIG. 1, the inertia body is at the back provided with a retainer pin 16, with a head, which can be caught by a rocker arm 15 at its one end. The rocker arm 15, which turns round a pin in the casing, is spring loaded for introduction into the path of the retainer pin by means of a compression spring 14 which loads the other end of the arm so that the inertia body 5 is kept by the rocker arm 15.

Release of the impact hammer takes place by compressive stress of the rocker arm 15 against the spring 14. This stress takes place on a trigger part 13 forming the rear end of the tool 4. This trigger part is mounted axially displaceable in the casing 6 against the power of one or several compression springs 17. When the part 13 is pressed inwardly, the spring power from the springs 17 and 14 must be overcome before the rocker arm 15 swings out of its mesh with the pin 16 thereby releasing the inertia body which is driven forward by the spring 7 and thereby leads the piercing plug 2 out of the casing 6.

The piercing plug 2 is in the shown example a cylindrical body with a blunt front end 3, as shown in FIG. 2. During its penetration surfaces of fracture are produced in the material, for which reason the size of the piercing plug and the shape of the front end can be found out by way of experiments, dependent on the use of the tool.

The casing is provided with an opening or window 8, as shown in FIG. 1. This opening is located in such a manner that the penetration of the piercing plug into the material can be read off. The opening can suitably be provided with a scale 10, which scale can be replaceable dependent on the use of the tool and the nature of the material.

The retaining member can be stopped at the front end 9 of the tool, by means of an insertable pin 12, which can be manually inserted into the member. Hereby the retaining member is prevented from turning itself for replacement of the piercing plug by turning of the bushing which keeps the piercing plug 2, and the retaining member is held in the advanced position when using the tool as an awllike tool for informatory testing of the nature of the surface of the material when inserting the piercing plug into the material.

The front end 9 has been obliquely cut for formation of an oblique contact face 11. Two opposite oblique contact faces 11 have been shown and on the parts of the front end 9 having not been cut, one or several pins have been mounted, as can be seen in FIG. 2. These pins facilitate the insertion work, as they can get into the material and keep it during the trigging. If it is desired to drive in, in an inclined direction, i.e. not at right angles to the surface of the material, the contact faces are used for guiding the tool. This is particularly suitable to the purpose when examining buried piles, as hereby is avoided to have to remove unnecessarily large quanties of earth.

Reference is made below to FIG. 3, which shows the tool in use. The trigger is loaded by a manual pressure until overcoming of the said spring powers. This spring load is of a definite size in order to secure that the front end 9 of the tool possesses a finely tuned starting pressure against the material 1. This is a condition for comparability of the readings. It ensures that the piercing plug is always released at the correct point of time, viz. when the spring load has been overcome. During the penetration of the piercing plug into the material, surfaces of fracture are produced in the material dependent on its condition and nature. As the degree of penetration depends on all the factors ng of importance to the mechanical properties of the material the penetration is, therefore, a measure of the strength of the material. This strength can be read off directly after the impact, by observing the position of the inertia body through the opening 8 in the tool. In determining now the proportion by a given penetration and the strength of a body by way of experiment and mark it out on the scale, the tool can be used as a strength measurer.

The strength of a material e.g. a wooden material can be stressed by many sorts of disintegration. It is consequently extraordinarily important, that people in situ and immediately after the driving in can determine whether the material possesses the necessary strength. This applies to wiring work in wooden masts, foundations, pile structures etc. These measurings can be made by people without any special qualifications, and as the material is not interfered with, which could possibly weaken it, the determination of the strength is enormously suitable to the purpose.

Elongated casing 6 has a front end portion corresponding generally to front piece 9 and a rear end portion adjacent trigger 13. Inertia body 5 moves linearly between these frong and rear end portions under the force of spring means 7 having one end attached to the front end portion of casing 6 and its other end portion attached to inertia body 5. Piercing plug 2 is attached to inertia body 5 through the retaining member and is on the side of the inertia body facing toward the front end portion of the casing. Piercing plug 2 extends through the opening in the front end portion of the casing.

Rocker arm 15 defines latch means in the form of a latch member pivotally mounted within casing 6 adjacent the rear end portion thereof for cooperation with a latch engaging member defined by headed retainer pin 16 on inertia body 5.

The trigger means for releasing the inertia body is defined by trigger 13 in the form of an end cap on the rear end portion of casing 6. Manual force applied to the trigger acts on the tool in a direction for holding the front end thereof in firm engagement with the material being tested.

Selectively operable pin 12 defines keeper means mounted on casing 6 and cooperating with the piercing plug retainer on inertia body 5 to hold the inertia body in a forward position at the front end portion of the casing with piercing plug 2 fully extended through the front opening. This also holds the retainer against rotation for manually turning the bushing which holds the plug to the retainer. The bushing projects through the opening in the front end portion of the casing and this allows the plug to be easily changed.

The oblique surfaces shown at 11 in FIG. 1 facilitate positioning of the tool with its longitudinal axis inclined out of perpendicular relationship with the surface of the material being tested while maintaining the front end portion of the tool in firm engagement with the material.

The side window 8 in casing 6, through which the rear end of inertia body 5 is visible, is provided with indicia on either a cover or on the casing. This indicia indicates the strength of the material being tested by proportionality to the penetration depth of the piercing plug.

With inertia body 5 in its retracted position of FIG. 1, piercing plug 2 is completely retracted within casing 6 in longitudinally spaced relationship to the front end portion thereof. Release of the latch means allows spring 7 to pull the inertia body linearly toward the front end portion of the casing for extending the piercing plug through the opening in the front end portion and into the material being tested.

I claim:

1. Apparatus for measuring the strength of a material comprising: an elongated casing having front and rear end portions, an inertia body positioned in said casing for movement between said front and rear end portions, an elongated piercing plug attached to said inertia body toward said front end portion of said casing, an opening in said front end portion of said casing for extension of said piercing plug therethrough, spring means for driving said inertia body in a direction from said rear end portion toward said front end portion of said casing, latch means for latching said inertia body adjacent said rear end portion with said piercing plug completely within said casing in longitudinally spaced relationship to said front end portion, trigger means for releasing said latch means to free said insertia body for movement toward said front end portion under the force of said spring means to extend said piercing plug through said opening and drive same into a material against which said front end portion is positionable, and said trigger means being operative to release said latch means under influence of manual force applied thereto in a direction for urging said front end portion of said casing into engagement with a material whose strength is being tested.

2. The apparatus as defined in claim 1 wherein said latch means comprises a latch pivotally mounted within said casing adjacent said rear end portion thereof and said inertia body includes a latch engaging member, a latch spring for pivoting said latch into engagement with said latch engaging member, said trigger comprising an end cap on said rear end portion and being movable axially of said casing toward said front end portion thereof for releasing said latch from engagement with said latch engaging member.

3. The apparatus as defined in claim 1 including selectively operable keeper means on said casing engageable with said inertia body for holding same adjacent said front end portion with said piercing plug fully extended through said opening.

4. The apparatus as defined in claim 3 including a retainer carried by said inertia body having a turnable bushing for releasably attaching said piercing plug thereto, and said keeper means being engageable with said retainer for holding same against rotation with said bushing extending outwardly of said casing through said opening.

5. The apparatus as defined in claim 1 wherein said front end portion includes at least one outwardly projecting sharp point for holding said front end portion against a material whose strength is to be tested.

6. The apparatus as defined in claim 1 wherein said front end portion includes at least one oblique exterior surface to facilitate positioning of said front end portion against a material with the longitudinal axis of said casing inclined out of perpendicular relationship with the surface of the material.

7. The apparatus as defined in claim 1 including a side window in said casing through which said inertia body is visible, and indicia on said casing adjacent said window for indicating the strength of the material being tested in accordance with the longitudinal position of said inertia body relative to said window.

8. The apparatus as defined in claim 1 wherein said piercing plug has a blunt front end and is of substantially uniform cross-sectional shape and size along its entire length.

9. The apparatus as defined in claim 1 wherein said spring means comprises a tension spring connected to said front end portion and to said inertia body for pulling said inertia body in a direction from said rear end portion toward said front end portion.

10. A method for the non-destructive testing of wood to determine the impact strength thereof essentially independently of the moisture content, comprising driving a piercing plug having a blunt head into a body of wood substantially transverse to the grain thereof by imparting to said piercing plug a predetermined amount of kinetic energy to cause said piercing plug to penetrate said wood and rupture fibers thereof to produce surfaces of fracture as a result of dynamic bending stress and dynamic tensile stress of the wood fibers, determining the extent of penetration of said piercing plug into said wood, and determining from said extent of penetration the impact strength of said wood.

11. A method of testing wood for deterioration comprising driving a piercing plug having a blunt head into a body of wood substantially transverse to the grain thereof by imparting to said piercing plug a predetermined amount of kinetic energy to cause said piercing plug to penetrate said wood and rupture fibers thereof to produce surfaces of fracture as a result of dynamic bending stress and dynamic tensile stress of the wood fibers, determining the extent of penetration of said piercing plug into said wood, and determining from said extent of penetration the impact strength of said wood and the possible deterioration thereof.

* * * * *

UNITED STATES PATENT AND TRADEMARK OFFICE
CERTIFICATE OF CORRECTION

PATENT NO. : 4,182,163
DATED : January 8, 1980
INVENTOR(S) : Preben Hoffmeyer

It is certified that error appears in the above—identified patent and that said Letters Patent is hereby corrected as shown below:

Column 3, line 62: "ng" should be --being--.

Column 4, line 17: "frong" should be --front--.

Signed and Sealed this

Tenth Day of June 1980

[SEAL]

Attest:

SIDNEY A. DIAMOND

Attesting Officer

Commissioner of Patents and Trademark